US010456062B2

(12) United States Patent
Iannotti et al.

(10) Patent No.: US 10,456,062 B2
(45) Date of Patent: Oct. 29, 2019

(54) ALIGNMENT OF MANIPULABLE SENSOR ASSEMBLY

(71) Applicant: THE CLEVELAND CLINIC FOUNDATION, Cleveland, OH (US)

(72) Inventors: Joseph P. Iannotti, Strongsville, OH (US); Wael K. Barsoum, Bay Village, OH (US); Jason A. Bryan, Avon Lake, OH (US); Pete O'Neill, Shaker Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 1183 days.

(21) Appl. No.: 14/149,861

(22) Filed: Jan. 8, 2014

(65) Prior Publication Data

US 2014/0200440 A1     Jul. 17, 2014

Related U.S. Application Data

(60) Provisional application No. 61/751,436, filed on Jan. 11, 2013.

(51) Int. Cl.
*A61B 5/06* (2006.01)
*A61B 34/20* (2016.01)
*A61B 17/00* (2006.01)

(52) U.S. Cl.
CPC ............. *A61B 5/061* (2013.01); *A61B 34/20* (2016.02); *A61B 2017/00115* (2013.01); *A61B 2034/2065* (2016.02)

(58) Field of Classification Search
CPC . A61B 1/00193; A61B 5/0077; A61B 5/1079; A61B 2034/105
See application file for complete search history.

(56) References Cited

U.S. PATENT DOCUMENTS 5,562,448 A     10/1996  Mushabac
6,152,565 A *   11/2000  Liu ................. A61B 3/107
                                              351/212

(Continued)

FOREIGN PATENT DOCUMENTS

WO     2006089426 A1     8/2006
WO     2007113815 A2    10/2007

(Continued)

OTHER PUBLICATIONS

International Search Report and Written Opinion, dated Apr. 23, 2014, pp. 1-21.

*Primary Examiner* — Tse W Chen
*Assistant Examiner* — Jason M Ip
(74) *Attorney, Agent, or Firm* — Tarolli, Sundheim, Covell & Tummino LLP (57) ABSTRACT

A method for aligning a manipulable sensor assembly includes determination of a replica surface, which represents a field of view of a manipulable sensor assembly associated with an object when the object is located in a desired position and oriented at a desired orientation. Electromagnetic radiation and/or sound reflected from a surface of the region of interest is detected to provide a surface map of the region of interest, which is compared to the replica surface to determine a rotation and/or a translation for the manipulable sensor assembly to bring the surface map into alignment with the replica surface. The position and/or the orientation of the object are altered. The detection of reflected electromagnetic radiation or sound, comparison of the surfaces, and alteration of the position and orientation of the object are repeated until the surface map is in alignment with the replica surface.

12 Claims, 8 Drawing Sheets

(56) References Cited

U.S. PATENT DOCUMENTS

| | | | | |
|---|---|---|---|---|
| 6,594,516 B1* | 7/2003 | Steckner | ............... | G06K 9/3216 |
| | | | | 600/411 |
| 2003/0021453 A1* | 1/2003 | Weise | ................... | A61B 5/1178 |
| | | | | 382/128 |
| 2004/0019274 A1* | 1/2004 | Galloway, Jr. | ......... | A61B 90/36 |
| | | | | 600/425 |
| 2006/0221072 A1* | 10/2006 | Se | .......................... | G01C 11/06 |
| | | | | 345/420 |
| 2008/0024488 A1* | 1/2008 | Visser | ..................... | A61B 6/466 |
| | | | | 345/420 |
| 2011/0050848 A1* | 3/2011 | Rohaly | ................... | G06T 15/10 |
| | | | | 348/43 |

FOREIGN PATENT DOCUMENTS

| | | | |
|---|---|---|---|
| WO | 2011134083 | A1 | 11/2011 |
| WO | 2012113484 | A1 | 8/2012 |

\* cited by examiner

ALIGNMENT OF MANIPULABLE SENSOR ASSEMBLY

CROSS-REFERENCE TO RELATED APPLICATION

This application claims priority to U.S. Provisional Patent Application No. 61/751,436, filed Jan. 11, 2013, which is incorporated herein by reference in its entirety.

BACKGROUND OF THE INVENTION

Surgical planning is a preoperative method of pre-visualizing a surgical intervention, in order to predefine the surgical steps, often in the context of computer assisted surgery. In general, a three-dimensional image of a region of interest of the patient, for example, via magnetic resonance imaging (MRI) or computer tomography (CT), is utilized to plan a surgical intervention within the region of interest.

SUMMARY OF THE INVENTION

In accordance with an aspect of the present invention, a method for aligning a manipulable sensor assembly to a desired position and orientation is described. A model of a region of interest is constructed. A desired position and orientation for an object is defined relative to the region of interest. A replica surface is determined from the model. The replica surface represents a field of view of a manipulable sensor assembly associated with the object when the object is located in the desired position and oriented at the desired orientation. Either electromagnetic radiation or sound reflected from a surface of the region of interest is detected at the manipulable sensor assembly to provide a surface map of the region of interest. The surface map is compared to the replica surface to determine at least one of a rotation and a translation for the manipulable sensor assembly to bring the surface map into alignment with the replica surface. At least one of the position and the orientation of the object are altered according to the determined at least one of the rotation and the translation. The detection of reflected electromagnetic radiation or sound, comparison of the surfaces, and alteration of the position and orientation of the object are repeated until it is determined that the surface map is in alignment with the replica surface.

In accordance with an aspect of the present invention, a system for aligning a manipulable sensor assembly to a desired position and orientation is described. The manipulable sensor assembly is configured to detect one of electromagnetic radiation and sounds reflected from a region of interest to provide a surface map over an associated field of view. The surface map includes a plurality of feature vectors in a multidimensional space. A non-transitory computer readable medium stores a replica surface, defined as a plurality of feature vectors in the multidimensional space, representing an expected surface map within the field of view of the manipulable sensor assembly when the sensor assembly is located at the desired position and oriented at the desired orientation. A registration system is configured to compare the surface map and the replica surface to determine if the manipulable sensor assembly is located at the desired position and oriented at the desired orientation. A feedback component is configured to notify a user when the manipulable sensor assembly is located at the desired position and oriented at the desired orientation.

In accordance with an aspect of the present invention, an apparatus for indicating a desired position and orientation with respect to a patient tissue is described. A user interface by which the apparatus can be manipulated by the user is provided. A position indicator is carried by the user interface. The position indicator is indicative of a position of at least a portion of the apparatus with respect to the patient tissue surface. An orientation indicator is carried by the user interface. The orientation indicator is indicative of an orientation of at least a portion of the apparatus with respect to the patient tissue surface. A manipulable sensor assembly is carried by the user interface. The manipulable sensor assembly is operative to detect at least one of electromagnetic radiation and sound reflected from a surface of a region of interest of the patient tissue to provide a surface map of the region of interest. A registration system is configured to compare the surface map and a predetermined replica surface to determine if the manipulable sensor assembly is located at the desired position and oriented at the desired orientation. A feedback component is configured to notify a user when the manipulable sensor assembly is located at the desired position and oriented at the desired orientation.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
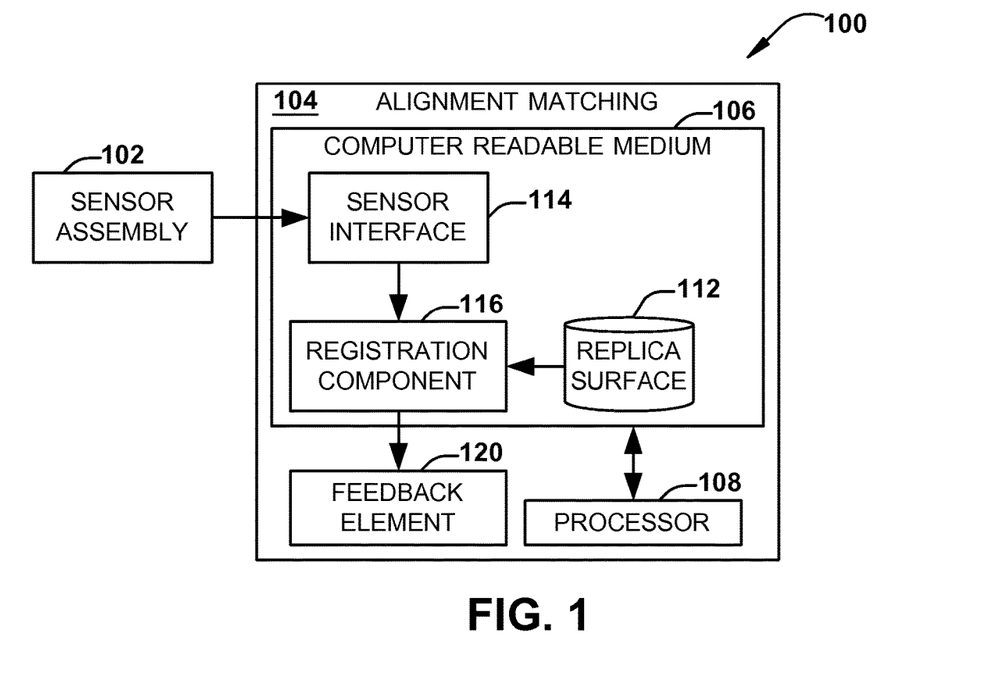
FIG. 1 illustrates a functional block diagram of an example system for aligning a manipulable sensor assembly to a desired position and orientation in accordance with an aspect of the present invention.

FIG. 1 illustrates a functional block diagram of an exemplary system 100 for aligning a manipulable sensor assembly 102 to a desired position and orientation in accordance with an aspect of the present invention. The manipulable sensor assembly 102 can include any sensor assembly that is manipulable by one or both of a human being or an automated system and is configured to detect at least one of electromagnetic radiation and sound reflected from a region of interest to provide a surface map over an associated field of view. For example, the sensor assembly 102 can be include at least one sensor configured to receive one or more of visible light, infrared light, ultraviolet light, and ultrasound and utilize an appropriate imaging method for determining a depth at each point on a surface such as structured light, white light interferometry, laser scanning, stereophotogrammetry, an acoustic imaging technique, or any other suitable means to provide a surface map comprising a plurality of feature vectors in a multidimensional space. It will be appreciated that the field of view and associated depth values will vary with the position and orientation of the sensor assembly 102.

The system 100 further includes an alignment matching element 104 implemented as machine executable instructions stored on a non-transitory computer readable medium 106 and executed by an associated processor 108. It will be appreciated, however, that the alignment matching element 104 could instead be implemented as dedicated hardware or programmable logic, or that the non-transitory computer readable medium 106 could comprise multiple operatively connected non-transitory computer readable media.

The non-transitory computer readable medium 106 stores a replica surface 112 as a plurality of feature vectors in a multidimensional space, representing an expected surface map within the field of view of the sensor assembly when the sensor assembly is located at a desired position and oriented in a desired orientation. In one implementation, the replica surface will be generated from a physical model of a region of interest, for example, by scanning a selected surface of the region of interest or a physical model generated from imaging data (e.g., via a rapid prototyping process) with the sensor assembly 102 or another sensor assembly. In another implementation, the replica surface can be extracted directly from a virtual model (e.g., mesh model, point cloud, or other virtual representation of one or more surfaces) of the region of interest. In still another implementation, the replica surface 112 can be generated dynamically from a physical model of the region of interest using a second manipulable sensor assembly (not shown).

During operation, the manipulable sensor assembly 102 images a surface of a region of interest and provides a set of vectors representing the imaged surface to a sensor interface 114 via an appropriate wired or wireless data connection. The captured sensor data and the stored replica surface 112 are provided to a registration component 116 that compares a set of received sensor data to the replica surface to determine at least one of a rotation and a translation for the manipulable sensor assembly 102 to bring the surface map captured by the sensor assembly 102 into alignment with the replica surface 112. It will be appreciated that the rotation can include changes in one or more of the pitch, roll, and yaw of the manipulable sensor assembly and/or precession of the manipulable sensor assembly about a remotely located center point. In one implementation, the comparison is performed via a point cloud registration process. For example, the point cloud registration process can include any of iterative closest point matching, coherent point drift, and robust point matching. The manipulable sensor assembly 102 will be assumed to be in the desired position and orientation when the sensor data matches the replica surface 112 within a predetermined threshold. In one implementation, the threshold is adjustable by a user to account for different tolerances in different applications. It will be appreciated that while the replica surface 112, sensor interface 114, and registration component 116 are shown as sharing a common computer readable medium 106, the components 112, 114, and 116 could be stored on multiple non-transitory computer readable media operatively connected to the processor 108 via a data bus or network connection.

A feedback element 120 is provided to communicate the determined rotation and translation to a manipulator of the manipulable sensor assembly 102. Where the manipulable sensor assembly 102 is a handheld device, the feedback element 120 can include a visible or audible indicator of the appropriate direction for movement or rotation of the device. Where the manipulable sensor assembly 102 is controlled by an automated system, the feedback element 120 can provide appropriately formatted machine readable instructions to the automated system to guide the manipulation of the sensor assembly.

Figure 2:
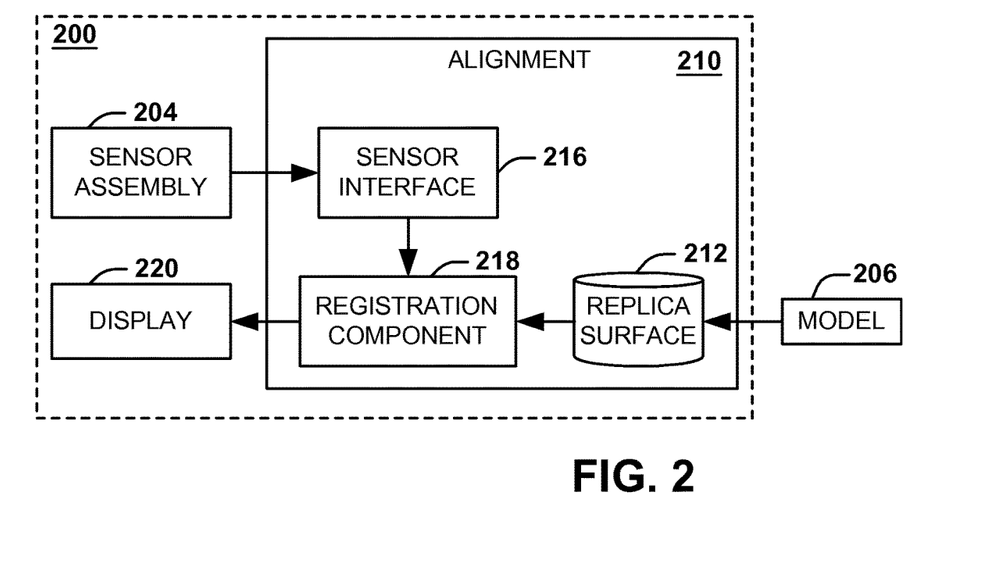
FIG. 2 illustrates a functional block diagram of an example implementation of a system for aligning a surgical tool to a desired position and orientation in accordance with an aspect of the present invention.

FIG. 2 illustrates a functional block diagram of an example implementation of a surgical tool 200 in accordance with an aspect of the present invention. The surgical tool 200 is manipulated by a user during a surgical procedure until the desired position or orientation is reached. It will be appreciated that a given user can include a medical professional, such as a surgeon, technician, or nurse, or an automated system (e.g., a robotic assembly). In the illustrated implementation, the surgical tool 200 includes a sensor assembly 204 and an alignment component 210. The manipulable sensor assembly 204 will have one or more sensors for receiving either sound or electromagnetic radiation reflected from a surface within the region of interest. In the illustrated implementation, the sensors include multiple visible light and/or infrared photosensors, although it will be appreciated that implementations with other electromagnetic radiation or sound may reasonably be made. The alignment component 210 can be implemented as dedicated hardware, machine readable instructions stored on a non-transitory computer readable medium and executed by an associated processor, or a combination of dedicated hardware and software.

A model 206 of a region of interest is used to generate a replica surface 212 for comparison, and the replica surface is stored on or at the alignment component 210. The model 206 is generated from imaging of the region of interest, and can represent a portion of tissue within the region. It will be appreciated that the model 206 can be a virtual model stored as computer readable instructions, for example, as a mesh model, or can be a physical model of the imaged region. In one implementation, the model 206 is a physical model created via a rapid prototyping process, such as three-dimensional printing. In another implementation, the model 206 can comprise the region of interest itself.

Prior to a surgical procedure, the user can select a location on the model 206 and orient the surgical tool 200 in the manner in which it would be oriented during a given step in the surgical procedure. When the tool 200 is in the desired position and orientation, a portion of the surface of the model 206 that is within an associated field of view of the sensor assembly 204 can be captured and recorded as the replica surface. In another implementation, the system 200 can be used to reacquire a position and orientation over a surface of the region of interest during the procedure. In this case, the tool 200 is manipulated to the desired position and orientation relative to the region of interest, and "zeroed" to capture the corresponding surface as a replica surface. At a later point in the surgical procedure, the captured surface can be used to require the desired position and orientation.

In accordance with an aspect of the present invention, multiple replica surfaces 212 can be generated for a given procedure, either from a single virtual or physical model 206 or from multiple models. Specifically, each of the replica surfaces can represent the expected condition of the region of interest after a given step of the surgical procedure. This can be accomplished, for example, by generating multiple physical models, each representing a stage in the procedure, updating a virtual model with emulated tissue alterations, or by altering a suitable physical model in a manner consistent with the operations. From each model, or each step in a series of alterations to a given model, a replica surface for a given portion of the procedure can be generated.

The alignment component 210 further comprises a sensor interface 216 for receiving the surface map from the sensors. It will be appreciated that, in the illustrated implementation, the sensor interface 216 can receive inputs from multiple cameras of the sensor assembly 204 and generate a map of the surface via, for example, stereophotogrammetry. The generated surface map is then provided to a registration component 218 that compares the surface map to the replica surface. In the illustrated implementation, the comparison is performed via a point cloud registration. From the comparison, it is determined if the surface map matches the replica surface 212 within a predetermined tolerance, and, if not, at least one of an appropriate rotation or translation of the tool 200 is determined that would be expected to bring the surface imaged by the sensor assembly 204 into alignment with replica surface.

In accordance with an aspect of the present invention, the comparison can be weighted to allow certain portions of the replica surface 212 to have a greater influence on the comparison result than other portions. For example, these portions of the surface can be identified by a surgeon, technician, or other expert in advance of the procedure, and communicated to the system 200 via an appropriate user interface. In one implementation, regions of the surface corresponding to areas of the region of interest that will be altered can be weighted as to contribute nothing to the comparison, such that the surfaces are matched only from the unaltered portions of the surface. Alternatively, where the replica surface 212 is generated from models formed via emulated tissue alterations, the emulated portion of the replica surface can be weighted to contribute less to the comparison. It will therefore be appreciated that the illustrated system 200 can be made robust against changes in surface topography, allowing for its use during later portions of a surgical procedure. In some implementations, even regions without significant tissue modification can be excluded from comparison to allow for a more efficient comparison of smaller data sets representing particularly significant structures.

The results of the comparison are communicated to the user at a display 220. The display can include, for example, a video screen that displays pictorial (e.g., arrows) or text messages to the user to inform the user of the determined rotation or translation. Alternatively, a series of LED lights and/or an audible signal (potentially varying in pitch) can be used to indicate whether to move or incline the device in a specific direction. Once the display indicates that alignment is achieved, the user can proceed with a task, such as implantation of a guide pin, associated with the desired position and orientation.

Figure 3:
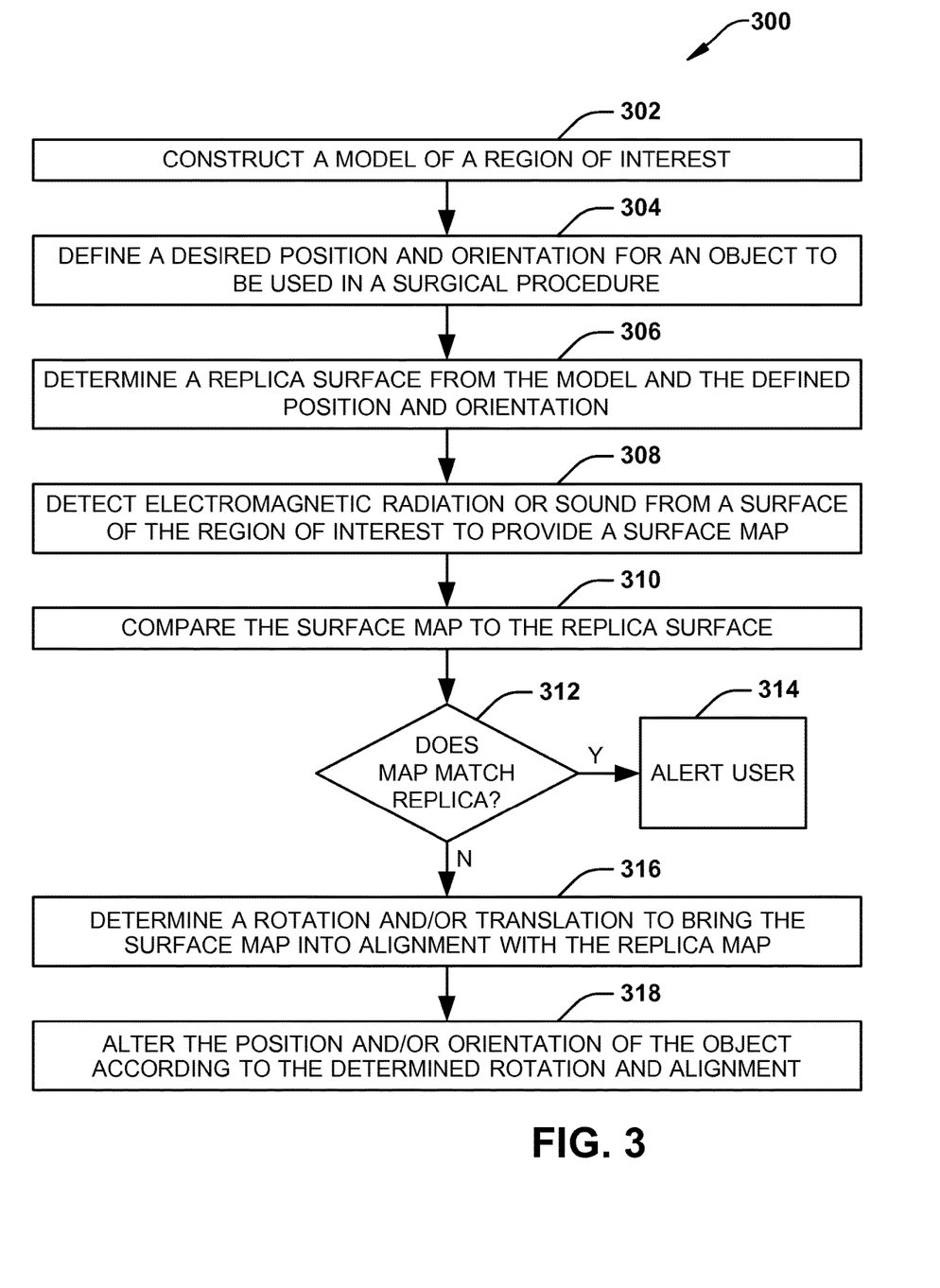
FIG. 3 illustrates a methodology for aligning a manipulable sensor assembly to a desired position and orientation in accordance with an aspect of the present invention.

In view of the foregoing structural and functional features described above, a method in accordance with various aspects of the present invention will be better appreciated with reference to FIG. 3. While, for purposes of simplicity of explanation, the method of FIG. 3 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 3 illustrates a methodology 300 for aligning a manipulable sensor assembly to a desired position and orientation in accordance with an aspect of the present invention. At 302, a model of a region of interest is constructed from imaging data of a region of interest. In general, the model will be constructed from data provided from an appropriate three-dimensional medical imaging system, such as computed tomography (CT) or magnetic resonance imaging (MRI). It will be appreciated that the model can be a virtual model, stored on a non-transitory computer readable medium, or a physical model produced via an appropriate manufacturing technique from the imaging data.

At 304, a desired position and orientation is defined for an object to be used in a surgical procedure. For example, a user or other medical professional can review the model and determine a position and orientation of the object that would be appropriate during a given portion of the surgical procedure. At 306, a replica surface is determined from the model. The determined replica surface represents a field of view of a sensor assembly associated with the object when the object is located in the desired position and oriented at the desired orientation. In one implementation, this is done by extracting the appropriate portion of the surface of a visual model as a series of vectors representing the position of points on the surface from an origin defined by the desired position and orientation. Alternatively, the object, or a surrogate object having a similar sensor assembly can be positioned over a physical model in the desired position and orientation, and a surface detected by the sensor assembly can be recorded as the replica surface. In general, steps 302, 304, and 306 will often occur prior to the surgical procedure, although it will be appreciated that a surrogate device (e.g., a physical model of a patient tissue), outfitted with an appropriate sensing assembly can be used to dynamically capture one or more replica surfaces during a procedure.

At 308, at least one of electromagnetic radiation and sound reflected from the region of interest at the manipulable sensor assembly is detected to provide a surface map of the region of interest. In general, this will occur as the user is manipulating the object during the procedure, with the surface map representing a surface in a field of view of the sensor assembly on the object. In one implementation, ultrasound waves are emitted from a transducer assembly and a reflection from the surface is detected at the transducer assembly. In another implementation, reflected electromagnetic radiation is detected at a plurality of sensors. Depending on the imaging modality, any of structured light, laser scanning, white light interferometry, stereophotogrammetry, an acoustic imaging technique, or any other desired means for acquiring spatial data can be used to provide the surface map.

At 310, the surface map is compared to the replica surface, and at 312, it is determined if the surface map matches the replica surface. In one implementation, the replica surface is determined to match the surface map when a total error between the surfaces falls below a threshold value. It will be appreciated that the threshold value can be adjustable by a user. For example, if the threshold is too small, it is possible that the device could deviate between a matched and an unmatched condition based only on small micromotions of the hand. If it is too large, precision is lost. Accordingly, in procedures in which exactness is particularly critical, the allowable error can be decreased, whereas in surgeries where the margin for error is greater, the allowable error can be increased so as to allow the device to be used easier in obtaining that match.

If the surfaces are determined to match (Y), the user is alerted to the match at 314. If the surfaces do not match (N), the method proceeds to 316, where one or both of a rotation and a translation are determined for the object to bring the surface map into alignment with the replica map. In one implementation, the determination is made via a point cloud registration technique. At 318, at least one of the position and the orientation of the manipulable sensor assembly are altered according to the determined at least one of the rotation and the translation. For example, visible or audible feedback can be provided to the user to inform the user of the necessary rotation and/or translation. Alternatively, machine readable instructions can be provided to an automated system to instruct the automated system to perform the determined rotation and/or translation. The method then returns to 308 to capture another surface map from the region of interest.

Figure 4:
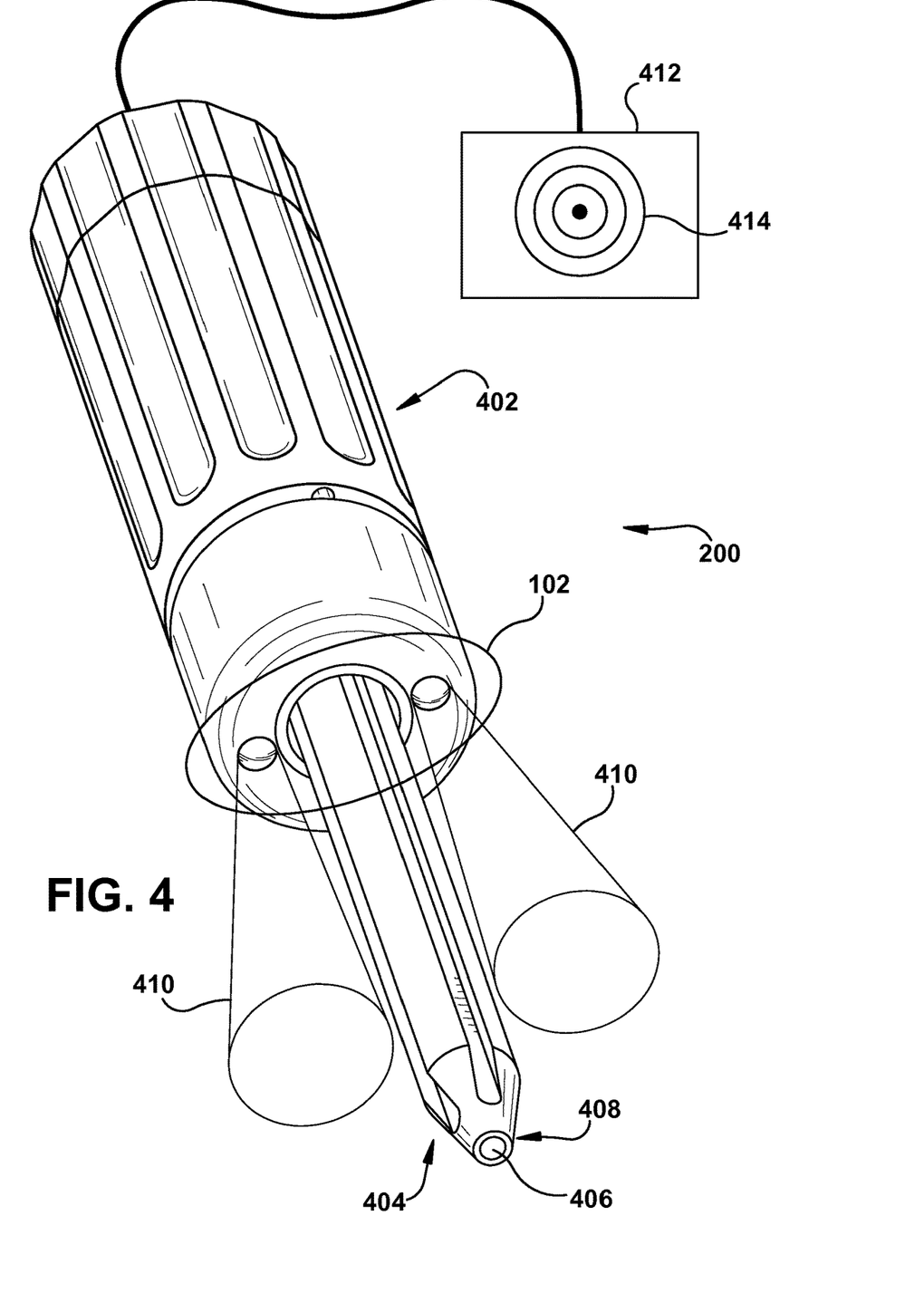
FIG. 4 is a perspective bottom schematic view of an apparatus according to an embodiment of the present invention.

FIGS. 4-7E illustrate an example of an apparatus which can be used to implement a method similar to that shown in FIG. 3 and described above. A surgical tool 200 shown in FIG. 4 is an example of a surgical device which can be used with the present invention. (The term "surgical device" is used herein to indicate any tool, prosthesis, natural or artificial patient tissue, or any other structure, device, or component for which it is desired to know and/or dictate a location and/or orientation with respect to a patient tissue.) The surgical tool 200 shown in FIG. 4 is a wire guide having a similar form factor to that of a commonly available screwdriver, with a handle 402 carrying a shaft 404, the shaft and handle having a continuous throughbore 406 extending therethrough to direct a guidewire, K-wire, guide pin, or other three-dimensional landmark object (not shown) into an underlying patient tissue at a desired location and/or orientation.

In FIG. 4, the handle 402 of the surgical tool 200 acts as an interface by which the surgical tool can be manipulated by a user—here, the manipulation will likely be manual, but it is also contemplated that a manual/automatic hybrid or full automatic manipulation could also or instead be provided (e.g., through mating of the handle with a robotic arm). A tip 408 of the surgical tool 200, carried by the handle 402, acts as a position indicator, to indicate a position of at least a portion of the surgical tool with respect to the patient tissue surface. In the depicted surgical tool 200, this indication is made via contact (or near contact) of the tip 408 to a patient surface and the known physical relationships between the tip and the other portions of the surgical tool, which are rigidly attached together.

Similarly, the shaft 404 can act as an orientation indicator, being indicative of an orientation of at least a portion of the surgical tool 200 with respect to the patient tissue surface. In the depicted surgical tool 200, this indication is made via the three-dimensional orientation of the shaft 404 in space and the known physical relationships between the shaft and the other portions of the surgical tool, which are rigidly attached together.

A manipulable sensor assembly 102, which could be any single one or combination of the manipulable sensor assemblies described above or may be any other suitable type, is carried by the handle 402. As is represented by the cones of view 410 shown schematically in FIG. 4, the manipulable sensor assembly 102 shown is of a "downward looking" type. The cones of view 410 are shown in FIG. 4 as diverging from one another to both view separate portions of the surface of the region of interest—for example, in cases where three-dimensional surface mapping is performed via time-of-flight calculations using collimated light (e.g. laser) or acoustic waves. For a manipulable sensor assembly 102 which uses stereophotogrammetry or a similar stereo imaging technique, the cones of view 410 of that manipulable sensor assembly may be configured to at least partially overlap on the surface of the region of interest. For some types of manipulable sensor assemblies, a "focus length" or distance from the surface of interest may be significant to achieving desired results, and the user interface or some other structure of the surgical tool 200 used to hold the manipulable sensor assembly could be dimensioned/configured accordingly. In one implementation, an emitter is provided on one region of the tool 200 to provide a grid of infrared points, and an infrared sensor is provided on another region to map the surface using the provided points. One of ordinary skill in the art can provide, calibrate, and operate a manipulable sensor assembly for a particular use environment of the present invention. Regardless of how such is accomplished, the manipulable sensor assembly 102 is operative to detect at least one of electromagnetic radiation and sound reflected from a surface of a region of interest of the patient tissue to provide a surface map of the region of interest.

Figure 5:
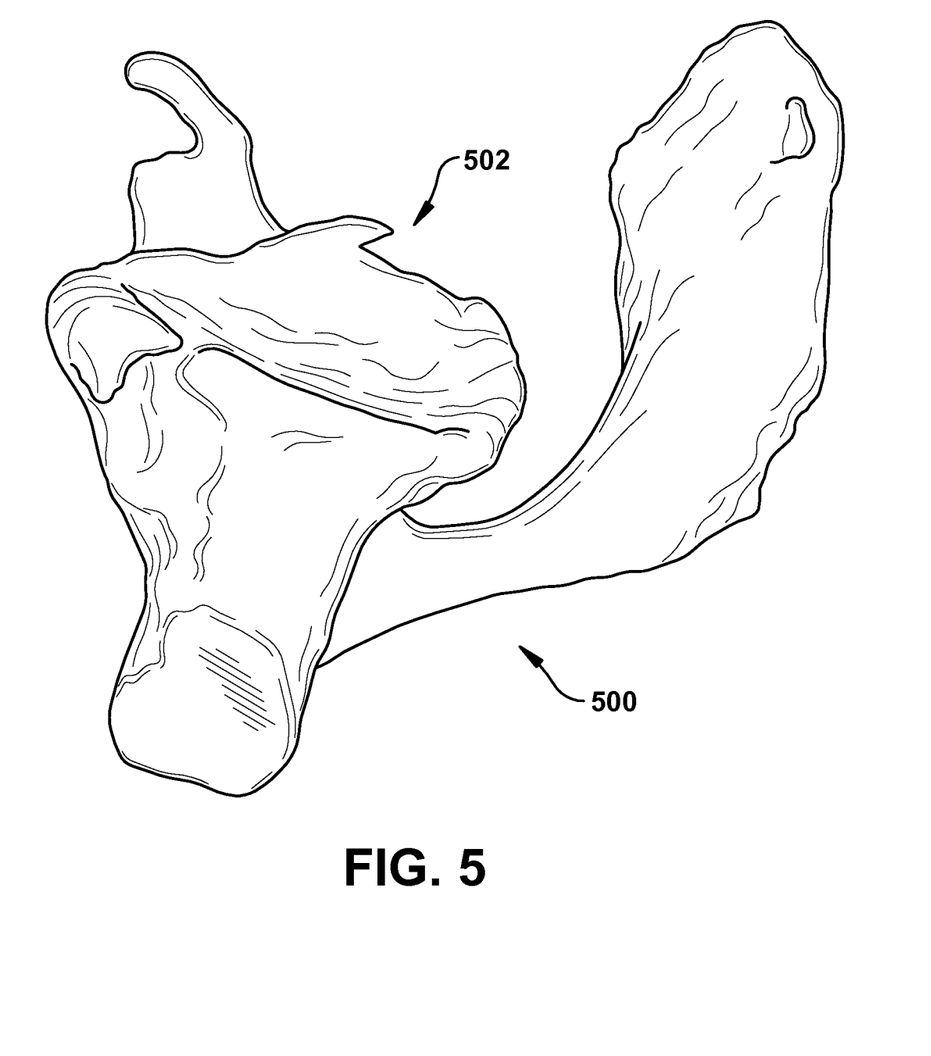
FIG. 5 is a perspective top view of an example use environment for the embodiment of FIG. 4.

In other words, an example patient tissue is shown in FIG. 5. The patient tissue shown and described herein is at least a portion of a scapula 500, but the patient tissue could be any desired type such as, but not limited to, hip joints, shoulder joints, knee joints, ankle joints, phalangeal joints, metatarsal joints, spinal structures, long bones (e.g., fracture sites), and deformable yet stable soft tissue (e.g., spleen, liver, and ocular tissues) or any other suitable patient tissue use environment for the present invention. The below description presumes that the system, apparatus, and method described is being used in conjunction with a surgical procedure (for example, an at-least-partial joint replacement or resurfacing), but the system, apparatus, and method described may be used in any desired manner and for any desired purpose without harm to the present invention.

A region of interest of the scapula 500 which will be used herein as an example is a glenoid 502, with a desired surgical task being characterized as placement of a guide pin into the glenoid 502 at a desired position and orientation. Accordingly the system 100 will need to be able to "see" the surface of the glenoid 502, create the surface map discussed previously, and guide the user to move the surgical tool 200 in relation to the glenoid until the surgical tool achieves the desired position and orientation, at which time the guide pin can be inserted through the throughbore 406 of the surgical tool and into the surface of the glenoid.

Figure 6:
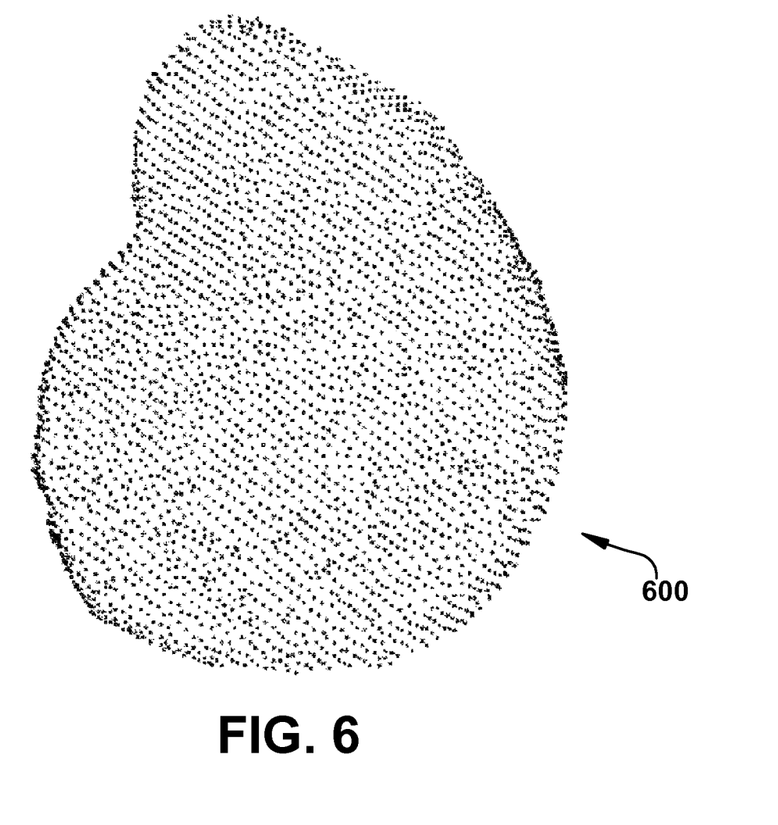
FIG. 6 is a visual depiction of a component of the present invention.

The surgical tool 200 or another component of the system 100 is provided with a predetermined replica surface as described above—that is, using any one or combination of a virtual model, a physical model, and an additional manipulable sensor assembly (not shown, but in communication with the manipulable sensor assembly 102) to acquire the predetermined replica surface. As shown in FIG. 6, the replica surface 600 is a three-dimensional representation of how the surface of the patient tissue will "look" to the manipulable sensor assembly 102 when that manipulable sensor assembly 102 has achieved a desired position and orientation with respect to the patient tissue. Through a known physical relationship (e.g., a direct physical correlation) between the manipulable sensor assembly 102 and other components of the surgical tool 200, the user can then be reasonably confident that placement of the manipulable sensor assembly at that desired position and orientation signals that other components (e.g., the throughbore 406) have also achieved their own desired position and orientation (which may be different from the desired position and orientation of the manipulable sensor assembly) with respect to the patient tissue.

To assist with use of the manipulable sensor assembly 102 in this manner, a registration system 412 (shown in FIG. 4) may be provided. The registration system 412 may be entirely carried on board the surgical tool 200 or could be at least partially remotely located and wired or wirelessly connected to the surgical tool, as shown schematically in FIG. 4. The registration system compares the instantaneous surface map (representing the real-time "view" seen by the manipulable sensor assembly 102) and the predetermined replica surface 600 to determine if the manipulable sensor assembly is located at the desired position and oriented at the desired orientation.

Like the registration system 412, a feedback component 414 may be entirely carried on board the surgical tool 200 or could be at least partially remotely located and wired or wirelessly connected to the surgical tool, with the feedback component 414 shown schematically in FIG. 4. The feedback component 414 is configured to notify the user when the manipulable sensor assembly 102 is located at the desired position and oriented at the desired orientation. In most use environments, the feedback component 414 will be configured to advise the user of a motion of the user interface which is intended to cause at least one of an instantaneous position and orientation of the manipulable sensor assembly 102 to approach the desired position and orientation of the manipulable sensor assembly. For example, with the feedback component 414 of FIG. 4 as an example, the user could be given a "bullseye" display with a dynamic indicator of the instantaneous position and/or orientation of the manipulable sensor assembly 102 relative to the desired position and/or orientation (at the center of the bullseye), such that the user can cause the dynamic indicator to approach the target center of the bullseye by moving the surgical tool with respect to the patient tissue.

In order to achieve the desired position and orientation of the manipulable sensor assembly 102 with respect to the patient tissue, the user may carry out a sequence similar to that shown schematically in FIGS. 7A-7E. While a cross-sectional or side view of the patient tissue is shown in FIGS. 7A-7E for clarity, it is contemplated that motion of the surgical tool 200 may occur three-dimensionally. In the sequence of FIGS. 7A-7E, it is presumed that the predetermined replica surface 600 has already been "saved" or "zeroed" by the system 100. It is also presumed that the user will have sufficient surgical exposure and manual dexterity, such as with the help of the handle 402, to place the manipulable sensor assembly 102 into an initial "start" position with respect to the patient tissue in which at least a portion of the instantaneous surface map "viewed" by the manipulable sensor assembly has some overlap with the stored replica surface 600.

Figure 7A:
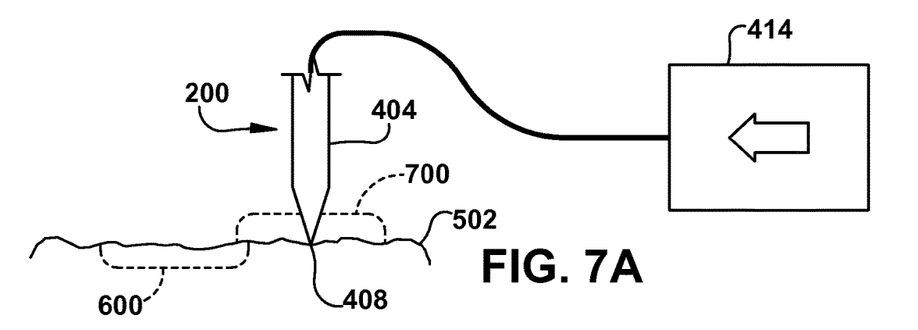
FIGS. 7A-7E illustrate a sequence of operation of the embodiment of FIG. 4.

In FIG. 7A, the surgical tool 200 has been placed into contact (or nearly enough into contact for purposes of the invention) with the glenoid 502. The dashed line at 600 represents the previously acquired/defined replica surface, and the dashed line at 700 represents the surface map. While these dashed-line constructs are shown here for explanatory purposes and will not normally be projected or actually superimposed on the physical components of the system 100 and/or the patient tissue, it is contemplated that certain embodiments of the invention could, indeed, use such projected representations to aid with the described method, either on the patient tissue and surgical tool 200 themselves or via a feedback component 414. The system 100 compares the replica surface 600 and the surface map 700 and presents to the user, via feedback component 414, an indication of the direction which the surgical tool 200 needs to move to approach the desired position and/or orientation. (Unlike the bullseye example in FIG. 4, the feedback component 414 in FIGS. 7A-7E uses directional arrows to communicate recommended translation motions to the user.)

This comparison and indication cycle, corresponding to at least a portion of the method shown in FIG. 3, may be of any desired length. For example, the cycle could be carried out almost continuously, to provide a relatively high resolution for the motion of the surgical tool 200. Alternately, a delay could be built in to the cycle, such that the cycle occurs, for example, every five hundred milliseconds (based upon the rate at which a human eye can detect visual changes), which could help conserve computing power in the system 100 while still providing relevant feedback to the user. Similarly, the cycle could be initiated by a triggering event, such as a rotational and/or translational motion of the surgical tool 200 above a predetermined threshold (e.g., detected by an accelerometer, not shown), or an action of the user (e.g., pressing a "check" button or tapping a tip 408 of the surgical tool lightly on the glenoid 502 surface). Optionally, the frequency at which the cycle is performed could be based upon how quickly the surgical tool 200 is being moved—if the movement is slow, the cycle could be performed less often—and/or how close the surface map 700 is approaching the replica surface 600—if the two are relatively highly correlated, the cycle could be performed more often. However, the sequence of FIG. 7A-7E is agnostic as to the cycle frequency.

Figure 7B:
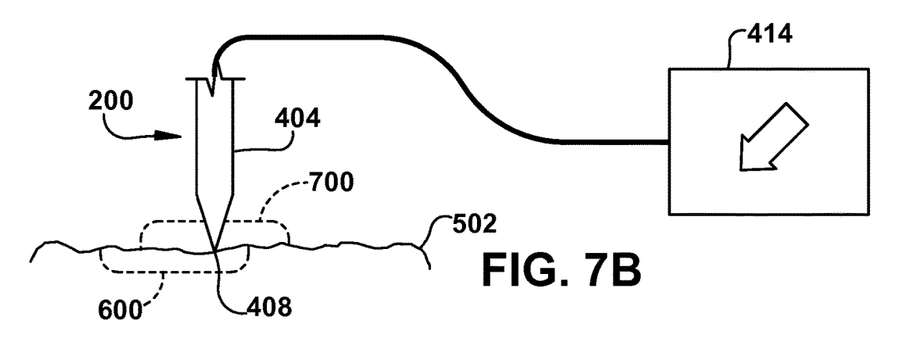

In FIG. 7B, the surgical tool 200 has been moved as recommended in FIG. 7A and the replica surface 600 and the surface map 700 have more overlap than in FIG. 7A. However, the system 100 has determined that additional motion is recommended and accordingly advises the user, via feedback component 414, of this additional motion. As shown in FIG. 7B, the recommended motion is angled, not orthogonal (X-Y), as was the recommended motion of FIG. 7A. It is contemplated that the recommended motion could be either a vector-type motion (a shortest distance between the current position of the surgical tool 200 and a desired position of the surgical tool in which the manipulable sensor assembly 102 will be in the desired position and orientation) or a stepwise, orthogonal-type motion in which a series of orthogonal movement recommendations are used to approximate a desired vector motion of the surgical tool. It is also contemplated that a combination of vector-type and orthogonal-type motions could be used to provide the desired recommended motions for a particular use environment of the present invention—e.g., vector-type motions for "coarse resolution" or large movements needed, and orthogonal-type motions for "fine resolution" or small movements needed as the replica surface 600 and the surface map 700 are brought closer to a correlated condition. In addition, the length, thickness, brightness, loudness (in the case of an audible cue), or some other perceptible property of the user interface of the feedback component 414 could be used to let the user know the magnitude of a recommended motion. For example, as shown in FIGS. 7A-7E, the arrows shown on the feedback component 414 could indicate the direction in which the surgical tool 200 should be moved, while the lengths of the arrows could indicate (either representationally/proportionally to exact values or schematically/approximately for generally "large" or "small" recommended motions) the magnitude of the recommended movement.

Figure 7C:
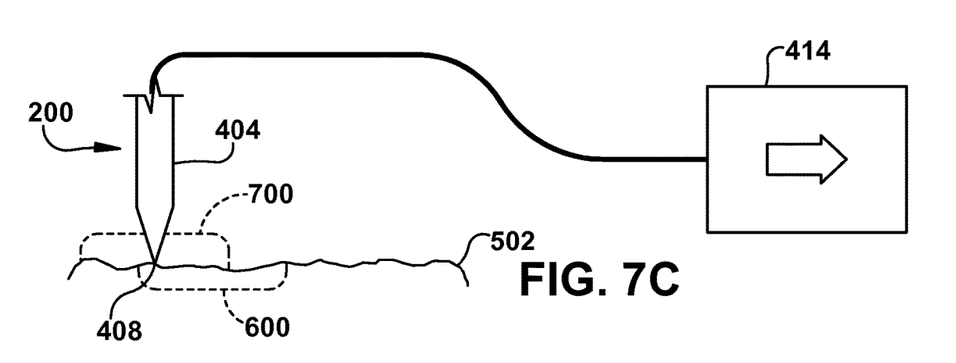

Regardless of the significance and information-containing aspects of the feedback component 414, however, a position of the surgical tool 200 is altered from the configuration of FIG. 7B to the configuration of FIG. 7C by movement of the surgical tool in the direction recommended in FIG. 7B. However, as seen by the comparison of the replica surface 600 and the surface map 700 in FIG. 7C, the surgical tool 200 has "overshot" the target, and the recommended motion in FIG. 7C is a "backwards" motion to correct that previous motion.

Figure 7D:
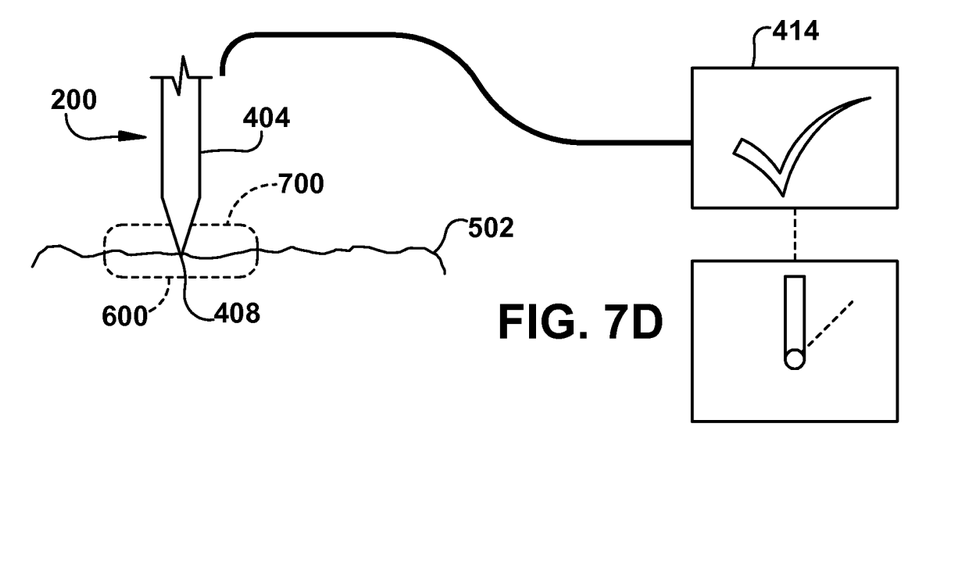

In FIG. 7D, the replica surface 600 and the surface map 700 have been deemed by the system 100 to be sufficiently aligned that at least one of the position and orientation of the manipulable sensor assembly 102 (and thus, in this example, the surgical tool 200) has achieved the desired position and orientation. A check mark or other "achieved" indication is given to the user via the feedback component 414 and the surgical procedure can proceed apace—such as via installation of the guide pin (not shown) through the throughbore 406.

Optionally, when the tip 408 of the surgical tool 200 has achieved the position upon the patient tissue surface shown in FIG. 7D, however, there may still need to be some rotation (which could include precession) of the surgical tool in place—this is especially likely if the comparison of the replica surface 600 and the surface map 700 in preceding cycles of the method, shown in FIGS. 7A-7C, are focused on translation motion. In such event, an optional additional "recommended rotation" indication may be made by the feedback component 414 itself and/or a secondary feedback component 414', as is shown in FIG. 7D by the relationship of the "actual rotation" dotted line to the "recommended rotation" solid block of the secondary feedback component. In FIG. 7D, the secondary feedback component 414' recommends a counterclockwise rotation of the surgical tool 200. For certain use environments of the present invention, it may be helpful to the user to separate the translational and rotational components of the recommended motions of the surgical tool 200, by recommending those motions sequentially and/or by using a secondary feedback component 414' (or a secondary function of the primary feedback component 414) to indicate the various translational and rotational motions recommended. Alternately, both translational and rotational motions could be recommended concurrently, particularly if the motions recommended are not overly complex or fine-resolution.

Figure 7E:
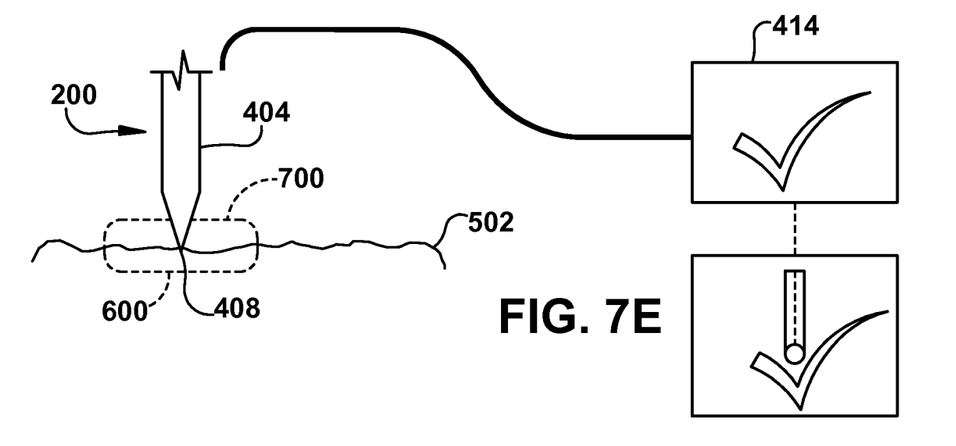

Finally, as shown in FIG. 7E, both the primary and secondary feedback components 414 and 414' show a "check mark" to indicate that the manipulable sensor assembly 102 (and/or some other portion of the surgical tool 200 to which the manipulable sensor assembly is attached) has achieved both the desired position and orientation with respect to the patient tissue. The user can then proceed with the procedure for which the position/orientation has been specified with a significant degree of confidence that the physical interactions are in compliance with a pre-operatively and/or intraoperatively specified surgical plan.

Figure 8:
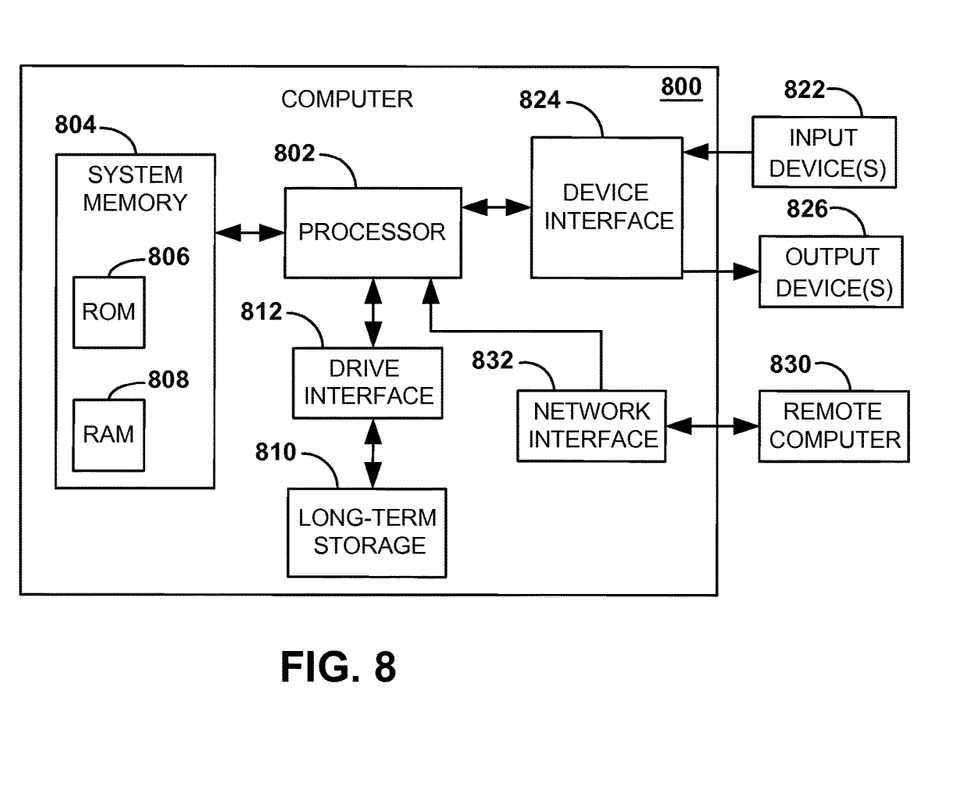
FIG. 8 illustrates a computer system that can be employed to implement systems and methods described herein.

FIG. 8 illustrates a computer system 800 that can be employed to implement systems and methods described herein, such as based on computer executable instructions running on the computer system. The user may be permitted to preoperatively simulate the planned surgical procedure using the computer system 800 as desired. The computer system 800 can be implemented on one or more general purpose networked computer systems, embedded computer systems, routers, switches, server devices, client devices, various intermediate devices/nodes and/or stand alone computer systems. Additionally, the computer system 800 can be implemented as part of a computer-aided engineering (CAE) tool running computer executable instructions to perform a method as described herein.

The computer system 800 includes a processor 802 and a system memory 804. Dual microprocessors and other multi-processor architectures can also be utilized as the processor 802. The processor 802 and system memory 804 can be coupled by any of several types of bus structures, including a memory bus or memory controller, a peripheral bus, and a local bus using any of a variety of bus architectures. The system memory 804 includes read only memory (ROM) 806 and random access memory (RAM) 808. A basic input/output system (BIOS) can reside in the ROM 806, generally containing the basic routines that help to transfer information between elements within the computer system 800, such as a reset or power-up.

The computer system 800 can include one or more types of long-term data storage 830, including a hard disk drive, a magnetic disk drive, (e.g., to read from or write to a removable disk), and an optical disk drive, (e.g., for reading a CD-ROM or DVD disk or to read from or write to other optical media). The long-term data storage 830 can be connected to the processor 802 by a drive interface 832. The long-term data storage 830 components provide nonvolatile storage of data, data structures, and computer-executable instructions for the computer system 800. A number of program modules may also be stored in one or more of the drives as well as in the RAM 808, including an operating system, one or more application programs, other program modules, and program data.

A user may enter commands and information into the computer system 800 through one or more input devices 822, such as a keyboard or a pointing device (e.g., a mouse). These and other input devices are often connected to the processor 802 through a device interface 824. For example, the input devices can be connected to the system bus by one or more a parallel port, a serial port or a universal serial bus (USB). One or more output device(s) 826, such as a visual display device or printer, can also be connected to the processor 802 via the device interface 824.

The computer system 800 may operate in a networked environment using logical connections (e.g., a local area network (LAN) or wide area network (WAN)) to one or more remote computers 830. A given remote computer 830 may be a workstation, a computer system, a router, a peer device or other common network node, and typically includes many or all of the elements described relative to the computer system 800. The computer system 800 can communicate with the remote computers 830 via a network interface 832, such as a wired or wireless network interface card or modem. In a networked environment, application programs and program data depicted relative to the computer system 800, or portions thereof, may be stored in memory associated with the remote computers 830.

It is contemplated that the system 100 and/or the apparatus described above may be integrated into a particular surgical device or may be separately provided for sequential use with multiple surgical devices. In the latter case, the system 100 and/or the apparatus may include a tool interface (e.g., a mounting bracket) which has a known physical relationship with both the surgical device and with the manipulable sensor assembly 102 for guiding the surgical device into a desired device position and a desired device orientation—which may be different from the desired position and orientation of the manipulable sensor assembly—with respect to the patient tissue.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the system 100 are merely illustrative; one of ordinary skill in the art could readily determine any number of tools, sequences of steps, or other means/options for placing the above-described apparatus, or components thereof, into positions substantively similar to those shown and described herein. The surgical tool 200 could include a low power "sleep" mode (automatically or manually induced) which conserves battery power if the surgical tool is not moved for a predetermined period of time. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. While some portions of the surgical tool 200 are shown and described as being rigidly connected together, it is contemplated that one of ordinary skill in the art would be able to design a surgical tool 200 or other surgical device with relatively moving components and perform appropriate offset sensing and calculations to translate the dynamic interactions of those relatively moving components to the static interactions of a rigidly connected device. Unless otherwise specifically stated, contact could be either direct or indirect. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A method for aligning a surgical tool, comprising a manipulable sensor assembly, to a desired position and orientation, the method comprising:
    defining a desired position and orientation for a tip of the surgical tool, rigidly attached to an end of a shaft of the surgical tool, relative to a region of interest;
    determining a replica surface as a plurality of vectors in a multidimensional space from the defined position, the defined orientation, and an associated model of the region of interest, such that the replica surface represents an expected surface map within a field of view of the manipulable sensor assembly, located on the surgical tool at a known position and orientation relative to the tip of the surgical tool, when the tip of the surgical tool is located in the desired position and oriented at the desired orientation; and
    iteratively repeating the following steps until the tip of the surgical tool is in the desired position and orientation:
        detecting one of electromagnetic radiation and sound reflected from a surface of the region of interest at the manipulable sensor assembly to provide a surface map of the region of interest, the surface map of the region of interest including a depth at each point on the surface at the region of interest;
        comparing the surface map to the replica surface to determine if the surface map matches the expected surface map represented by the replica surface;
        determining a rotation for the manipulable sensor assembly to bring the surface map into alignment with the replica surface if the surface map does not match the replica surface, wherein the rotation is determined from the known position and orientation of the manipulable sensor assembly relative to the tip of the surgical tool and the comparing of the surface map to the replica surface; and
        altering the orientation of the tip of the surgical tool according to the determined rotation if the surface map does not match the replica surface.

2. The method of claim 1, wherein defining the desired position and orientation for the tip of the surgical tool relative to the region of interest comprises constructing the model of the region of interest.

3. The method of claim 2, wherein constructing the model of a region of interest comprises generating a virtual model of the region of interest from medical imaging data and storing the virtual model on a non-transitory computer readable medium.

4. The method of claim 2, wherein constructing the model of a region of interest comprises generating a physical model of the region of interest from imaging data.

5. The method of claim 4, wherein determining the replica surface from the defined position and orientation comprises:
    positioning the tip of the surgical tool in the desired position and orientation relative to the physical model; and
    detecting one of electromagnetic radiation and sound reflected from a surface of the region of interest at the manipulable sensor assembly to provide the replica surface.

6. The method of claim 2, wherein constructing the model of a region of interest comprises generating a physical model of the region of interest as one of a mold and a cast of the region of interest.

7. The method of claim 1, wherein determining the rotation comprises using a point cloud registration technique.

8. The method of claim 1, detecting the one of electromagnetic radiation and sound reflected from the surface of the region of interest at the manipulable sensor assembly comprises:
    emitting ultrasound waves from a transducer assembly; and
    detecting a reflection from the surface at the transducer assembly.

9. The method of claim 1, wherein altering the orientation of the tip of the surgical tool according to the determined rotation comprises communicating the determined rotation to a human operator via one of a visible and an audible indicator, such that the human operator adjusts the orientation of the tip of the surgical tool.

10. The method of claim 1, wherein altering the orientation of the tip of the surgical tool according to the determined rotation comprises providing machine readable instructions representing the determined rotation to an automated system.

11. The method of claim 1, wherein comparing the surface map to the replica surface to determine the rotation for the manipulable sensor assembly comprises comparing a selected portion of the surface map, representing less than all of the provided surface map, to a corresponding portion of the replica surface, the selected portion being selected by a surgeon as a portion of the region of interest that will not be altered in a surgical procedure.

12. The method of claim 1, wherein determining the replica surface from the defined position and orientation comprises:
   positioning the tip of the surgical tool in the desired position and orientation relative to the region of interest; and
   detecting one of electromagnetic radiation and sound reflected from a surface of the region of interest at the manipulable sensor assembly to provide the replica surface.

* * * * *